United States Patent
Engelman

(10) Patent No.: US 7,682,322 B2
(45) Date of Patent: Mar. 23, 2010

(54) ARTICULATED ORTHOSIS PROVIDING LIFT SUPPORT

(76) Inventor: Ian K. Engelman, 3 Rhonda Dr., Scarborough, ME (US) 04074

( * ) Notice: Subject to any disclaimer, the term of this patent is extended or adjusted under 35 U.S.C. 154(b) by 659 days.

(21) Appl. No.: 10/562,944

(22) PCT Filed: Feb. 15, 2005

(86) PCT No.: PCT/US2005/005536
§ 371 (c)(1), (2), (4) Date: Dec. 29, 2005

(87) PCT Pub. No.: WO2006/088466
PCT Pub. Date: Aug. 24, 2006

(65) Prior Publication Data
US 2007/0265557 A1 Nov. 15, 2007

(51) Int. Cl.
A61F 5/00 (2006.01)
A61F 5/28 (2006.01)
A61B 19/00 (2006.01)
A61F 5/37 (2006.01)

(52) U.S. Cl. ............... 602/16; 602/5; 602/12; 602/20; 602/21; 602/23; 602/26; 602/27; 602/28; 128/103.1; 128/869; 128/878; 128/882

(58) Field of Classification Search ............ 602/5, 602/9, 12, 16, 19, 21, 23, 26–27; 128/103.1, 128/882
See application file for complete search history.

(56) References Cited

U.S. PATENT DOCUMENTS

| | | | |
|---|---|---|---|
| 3,976,057 A * | 8/1976 | Barclay | 601/34 |
| 4,289,122 A | 9/1981 | Mason et al. | |
| 4,665,904 A | 5/1987 | Lerman | |
| 4,732,143 A * | 3/1988 | Kausek et al. | 602/16 |
| 4,934,355 A * | 6/1990 | Porcelli | 602/16 |
| 5,044,360 A | 9/1991 | Janke | |
| 5,088,479 A * | 2/1992 | Detoro | 602/27 |
| 5,328,444 A * | 7/1994 | Whiteside | 602/16 |
| 5,399,149 A * | 3/1995 | Frankowiak et al. | 602/16 |
| 5,486,157 A | 1/1996 | DiBenedetto | |
| 5,496,263 A * | 3/1996 | Fuller et al. | 602/27 |
| 5,624,389 A * | 4/1997 | Zepf | 602/26 |
| 5,685,811 A * | 11/1997 | McShane et al. | 482/114 |
| 5,716,336 A * | 2/1998 | Hines et al. | 602/27 |
| 5,826,304 A | 10/1998 | Carlson | |
| 5,908,398 A | 6/1999 | DeToro | |
| 6,074,355 A * | 6/2000 | Bartlett | 602/16 |
| 6,080,123 A * | 6/2000 | Pansiera | 602/16 |
| 6,171,272 B1 * | 1/2001 | Akita et al. | 602/28 |

(Continued)

*Primary Examiner*—Patricia M Bianco
*Assistant Examiner*—Brandon Jackson
(74) *Attorney, Agent, or Firm*—Shalom Wertsberger; Saltamar Innovations

(57) ABSTRACT

An orthosis having at least one adjustable joint for articulating two hinged parts of the orthosis, the joint comprises a tensor for carrying the load applied between the two hinged parts. Compression surfaces coupled to the hinged parts are constructed to apply compression forces to a compression element when the angle between the two parts widens. Preferably the compression element comprises a block of resilient material. The joint allows adjustability of the unloaded angle between the hinged parts by varying the dimensions of the block, while selecting blocks having different compressional characteristics such as modulus of elasticity allows varying the degree of resistance to widening the angle between the two hinged parts. The joint is particularly advantageous in constructing an articulating leg brace.

16 Claims, 9 Drawing Sheets

U.S. PATENT DOCUMENTS

| | | | |
|---|---|---|---|
| 6,245,034 B1 * | 6/2001 | Bennett et al. | 602/20 |
| 6,409,695 B1 * | 6/2002 | Connelly | 602/27 |
| 6,527,733 B1 * | 3/2003 | Ceriani et al. | 602/16 |
| 6,666,837 B2 * | 12/2003 | Weihermuller | 602/16 |
| 6,689,081 B2 | 2/2004 | Bowman | |
| 6,824,523 B2 * | 11/2004 | Carlson | 602/16 |
| 7,192,407 B2 * | 3/2007 | Seligman et al. | 602/16 |
| 2003/0158506 A1 * | 8/2003 | Hinshon | 602/16 |

* cited by examiner

ARTICULATED ORTHOSIS PROVIDING LIFT SUPPORT

FIELD OF INVENTION

The present invention relates generally to orthotic braces and more particularly to articulated braces having a joint with adjustable lift assist.

BACKGROUND

There are many pathologies that can lead to loss of function of the foot and ankle. By way of example, these include stroke, diabetes, Muscular dystrophy, multiple sclerosis and peripheral vascular disease, as well as others. Often the biomechanical deficit will involve loss of dorsiflexion, i.e. the loss of ability to bring the foot up. This situation is generically known as drop foot.

The traditional solution is to provide a brace commonly known as an Ankle Foot Orthosis (AFO). The orthosis is commonly made out of one piece of plastic which is trimmed in the back so that it becomes flexible. This design is commonly known in the art as a Posterior Leaf Spring AFO.

An improved orthosis is an articulated AFO. This orthosis has an upper portion (calf section) connected to a lower portion (foot section) by a joint. The joint is internally or externally spring loaded so that it picks up the foot. For a spastic patient, a range limiting joint design may be indicated. A range limiting joint limits the patients' ability to push the foot down (plantarflex) beyond a predetermined angle. The articulated design allows a better biomechanical movement of the foot.

U.S. Pat. No. 5,826,304 to Carlson describes a composite flexure unit for hingedly joining two relatively movable parts. The unit includes a flexure member comprising a low modulus of elasticity material. The flexure has two mounting portions and a middle connecting portion. The flexure is bendable for pivoting about a rotational axis passing through the middle portion. A load bearing element comprises a high modulus of elasticity material for providing longitudinal strength and stiffness, without significantly increasing flexion stiffness about the rotational axis. An improvement over the Carlson patent is known and marketed under the trade name Tamarak Variable Assist™ Joint, (available from Tamarack Habilitation Technologies, Inc, Blaine, Minn., USA) wherein an adjustable hinge is added to one of the mounting portions, to allow mounting the flexure unit at adjustable angles to a portion of the brace.

U.S. Pat. No. 4,665,904 to Lerman discloses a supportive brace includes lateral and medial circular hinges rotatably securing the lateral and medial sides of the leg-supporting shell to the foot supporting shell. The circular hinges are formed by relatively large area wall portions of the shells which overlie each other in the vicinity of the ankle bones projected from the lateral and medial sides of the ankle.

It is therefore desired to provide a mechanism of adjustability of the joint characteristics that can easily tailored to individual patient needs such for example by the health care practitioner. Two degrees of adjustability are desired: the angle from which the plantarflexion preloading begins and the moment of force that is created from the preloading. An articulated AFO design that allows this adjustability is biomechanically desired for two important reasons: shock absorption at heel contact and knee stability at heel contact. During ambulation the first part of the step is when the heel hits the ground and the foot plantarflexes to what is generally referred to as footflat. At that first part, it is desirable to adjust the amount of resistance to plantarflexion according to individual needs, as without such resistance there is little to no shock absorption. On the other hand, an excessive resistance to plantarflexion will force the knee forward, resulting in a less stable biomechanical situation. The present invention provides easy adjustability, in an easy to manufacture design, which is cost efficient to manufacture.

An orthosis made of two parts presents a problem where, upon sliding the foot into the orthosis, the foot painfully hits, or otherwise gets snagged by, the foot portion. Certain aspects of the present invention aim to resolve this problem.

BRIEF DESCRIPTION

The present invention provides an articulated AFO or other orthosis, wherein the joint has a combination of a tension element (equivalently called a tensor hereinafter) and an elastic compression element that is being compressed by at least a pair of compression surfaces attached to the foot portion and the calf portion respectively. When applied to any articulating orthosis other than an AFO, the hinged parts of the orthosis are considered the portions equivalent to the calf portion and foot portion.

By modifying the dimensions of the compression element, there is provided a field adjustable preloading, i.e. an adjustable angle at no load or light load conditions. Similar effect may be obtained by adjusting the effective length of the tensor. Adjustment of dorsiflexion moment is achieved by modifying the size, shape, or the elastic characteristics of the compression element. The present invention is equally applicable both to custom made and to pre-fabricated braces. By using a flat tensor a 'foot funnel' is created that eases donning the brace by providing surfaces that prevent the interference between the foot and the lower part of the brace as described above.

Therefore in accordance with a preferred embodiment of the invention, there is provided an articulated orthosis having a first and a second hinged parts, the orthosis having an inner and outer surfaces, and at least one joint for hinging the first and second part. The orthosis comprises a tension element having a first anchor point coupled to the first hinged part and a second anchor point coupled to the second hinged parts, the tension element having at least one flat outer surface which is substantially parallel to the inner surface of the orthosis adjacent to the tension element. Further provided are a first and a second compression surfaces coupled to the first and second parts respectively, with a compression element disposed between the compression surfaces wherein the compression surfaces are located so as to transmit forces to the compression element as a result of angular motion between the first and second hinged parts, the forces being operable to compress the compression element.

Preferably, the compression element comprises a first block of resilient material. Also preferably, the flat surface of the tensor is co-planar with the inner surface to provide a better 'foot funnel'.

At an unloaded condition the preload angle between the first and second hinged parts is variable by the dimensions of the compression element. Preferably the tension element has an adjustable effective length, for allowing relative lateral or medial adjustment of the hinged parts, as well as an additional method of controlling the preload angle. The resistance to moment force applied to at least one of the hinged parts is variable by the modulus of elasticity of the compression element.

In the preferred embodiment at least one of the hinged parts has a plurality of retaining walls for forming a chamber to at least partially contain the compression element. The tension element (equivalently referred to as a tensor) defines a boundary of the chamber. Most preferably, a part of the chamber is formed in the first hinged part, and another part is formed in the second hinged part, and the compression surfaces comprise a part of the chamber, such as one or more of the walls defining the chamber.

Optionally, at least one of said retaining walls is movable for changing the dimensions of the chamber, for allowing field adjustment of the joint characteristics such as pre-load and/or resistance to moment force. Also optionally, at least one of the compression surfaces is adjustable.

Optionally, the compression element further comprises a second block of resilient material having a higher modulus of elasticity than the modulus of elasticity of the first block, the second block disposed between at least a portion of the first and second hinged parts, so as to be compressed as result of angular motion therebetween, after compression has been applied to the first block. This results in a 'stop block', which limits the relative movement of the hinged parts, while providing a soft rather than an abrupt stop.

For ease of manufacturing the tension element preferably comprises anchor points transverse to the flat side.

Preferably the tensor has an overall bending stiffness of between 0.035 and 1.3 Nm (Newton meter). More preferably, the tension element has an overall bending stiffness of between 0.08 and 0.9 Nm. Most preferably, the tension element has an overall bending stiffness between 0.2 and 0.5 Nm.

An alternative compression element may be selected from a list consisting of a spring, jell cell, pneumatic container, hydraulic cell, or a combination thereof.

In another aspect of the present invention there is provided an articulated orthosis having a first and a second hinged parts, the orthosis having an inner and outer surfaces, and at least one joint for hinging the first and second part. The orthosis comprises a first and a second compression surfaces coupled to the first and second parts respectively, and a plurality of retaining walls coupled to at least one of the hinged parts, the walls defining a chamber. Preferably, the compression surfaces are integrated in the chamber. A compression element that is at least partially disposed within the chamber, and a tension element which is at least at least partially disposed within the chamber, the tension element comprises a first anchor point coupled to the first hinged part and a second anchor point coupled to the second hinged parts. The compression surfaces are located so as to transmit forces to the compression element as a result of angular motion between the first and second hinged parts, the forces being operable to compress the compression element. Preferably, the compression element comprises a first block of resilient material, however as in the previous case, it may is selected from a list consisting of a spring, jell cell, pneumatic container, hydraulic cell, or a combination thereof.

Optionally, the tension element is retained in place by forces applied by the compression element. Further optionally, the tension element comprises at least one support, which interacts with the compression element to retain the compression element in place.

A potential application for the invention is in the design of a wrist hand orthosis. Like the foot, pathologies may make it difficult or painful to extend the wrist in order to raise the hand. The articulated design connects the upper section (forearm section) to the lower section (hand section) in order to provide lift assist to the hand. The range limiting feature may also be desirable for certain treatment options. The skilled in the art will see that the teachings provided herein easily and clearly extend to a wrist hand orthosis.

BRIEF DESCRIPTION OF THE DRAWINGS

Different aspects of preferred embodiments of the invention will be better understood in view of the accompanying drawings, in which.

DETAILED DESCRIPTION

Different aspects of the invention are described in terms of an AFO, which is the preferred embodiment, however it will be clear to the skilled in the art that the invention extends to other orthosis requiring adjustability in pre-loading and moment. Some preferred embodiments are described below.

Figure 1:
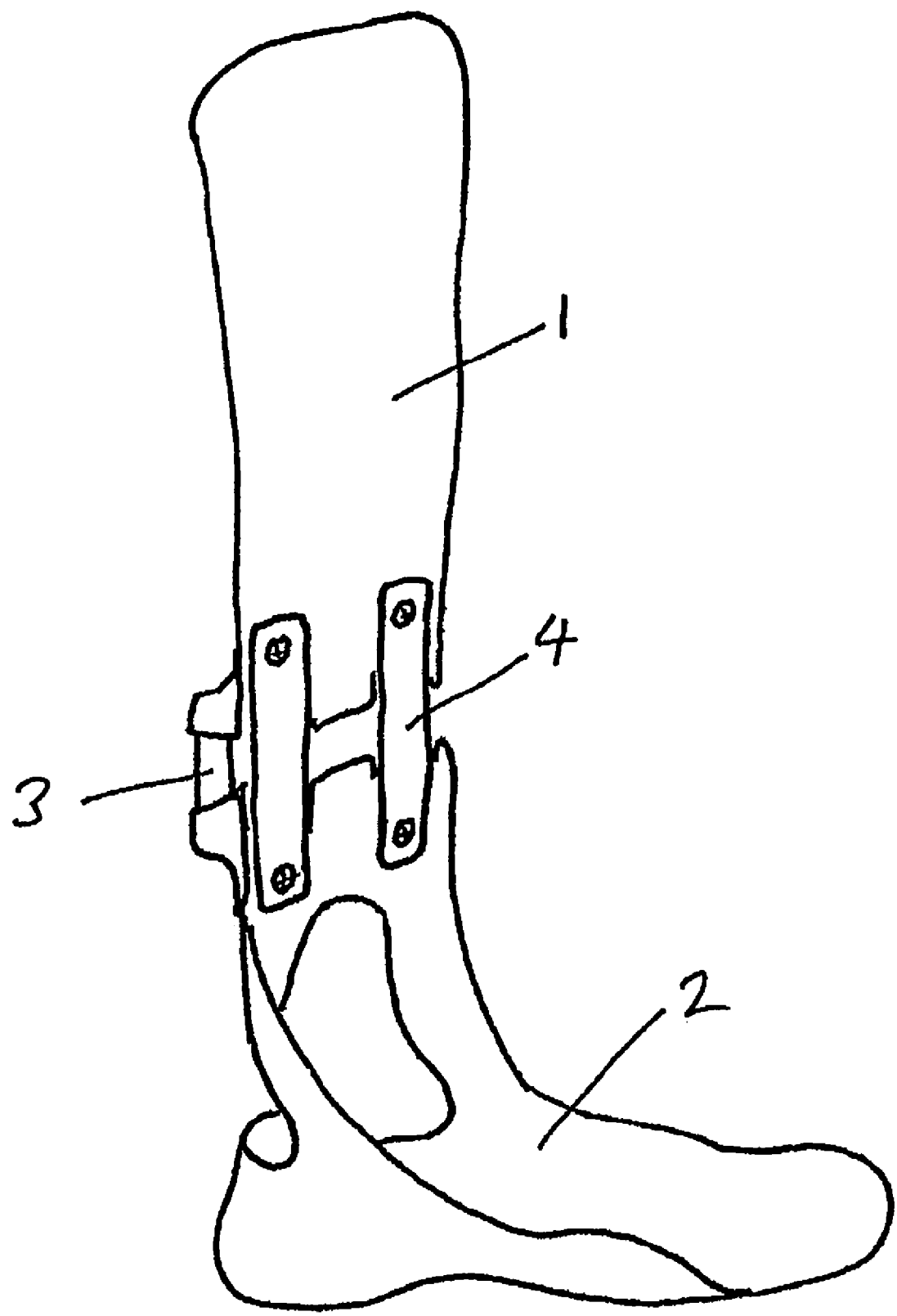
FIG. 1 is a general depiction of an articulated brace.

FIG. 1 is a general depiction of an ankle foot brace. A calf section 1 is articulated to a foot section 2 through two joints 3 and 4 respectively. While a single joint brace is also useful, the preferred embodiment calls for utilizing two joints.

Figure 2:
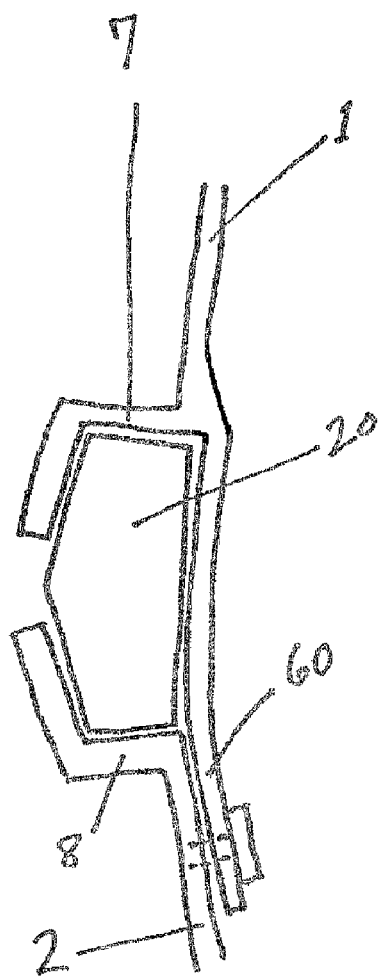
FIG. 2 depicts a cross section of a preferred embodiment of the joint in an unloaded state.

FIG. 2 depicts a cross section of the preferred embodiment of the invention in an unloaded state. The calf portion 1 and the foot portion 2 of the brace, each have a compression surface 7 and 8 respectively. A tensor 60 is coupled to the calf portion and to the foot portion and holds the portions together. In the preferred embodiment the tensor is coupled using fasteners, such as screws, rivets and the like. The tensor is made of resilient material having relatively high tensile strength in at least one plane.

The tensor is sufficiently stiff to resist unwanted over flexion, yet sufficiently flexible to allow for a full range of motion. This effect is achieved by a quality described as overall bending stiffness. Bending Stiffness is described by EI, the product of Young's modulus of elasticity (E) and the second moment of inertia (I). In other words, the bending stiffness of the tensor can be varied by changing the material (thus modulus of elasticity) or the shape (or size) of the cross section of the tensor. The values presented in these specifications for overall bending stiffness are values of bending stiffness (EI) divided by the length of the tensor (L) [overall bending stiffness=EI/L]. The values presented are for tensors with a consistent cross section throughout the length of the tensor. It will be clear to the skilled in the art that equivalent overall bending stiffness may be achieved with an infinite range of various cross sections within the length of the tensor. The preferred embodiment will use tensors having varying cross section to better support the mounting points.

As mentioned above, a common problem during donning an AFO is interference between the foot and foot section. A common way of donning the brace involves sliding the foot from the calf section to the foot section. Therefore it is desirable to provide support for the foot as it slides down the brace creating a 'foot funnel' to assist in donning. In the preferred embodiment the tensors are located on the inside surface of the brace, and therefore provide a continuity, over which the foot glides as it is being inserted into the brace. It is therefore clear why the preferred embodiment uses a generally flat tensor, mounted with its flat side mounted substantially parallel to the inner surface of the brace, and most preferably coplanar therewith. Thus the tensors of the joint create a "slide" that bridges the gap between the calf section and the foot section. This provides a smooth 'foot funnel'. It is noted however that other tensor cross sections are also applicable. Placing of the joint posterior superior to the ankle joint further assists in creating such a 'foot funnel'. Furthermore, the preferred embodiment would comprise one or more of the tensors be an integral part of the calf section, thus providing a smoother 'foot funnel' effect.

Preferably, the tensor has several anchor points to vary its length and thus the distance between the calf portion and the foot portion. In the preferred embodiment, the tensor is flat, and the anchor points are drilled through the flat side, i.e. the anchor points are transverse to the flat side, therefore allowing easy mounting of the tensor to the foot and calf portions, while crating the 'foot funnel' described above. Alternatively, different sizes of tensors may be provided, and/or a plurality of anchor points may be provided in the brace shell.

A compression element 20 (equivalently referred to as a bumper in these specifications) is disposed between the two compression surfaces 7 and 8. The bumper 20 may be held in place by any desired method, such as glue, fastener, strap and the like, but the most preferred embodiment calls for a chamber bounded by side walls and top walls 5 and 15 integral to the brace sections, and the tensor 60. Such chamber holds the bumper securely and limits the movement of the bumper during both compressed and free states. Most preferably the chamber is formed in two parts, divided between the calf portion and the foot portion, each formed integrally into the respective brace portion. This construction allows for a strong support to the compression surfaces 7 and 8 that constitute one wall of the chamber. The chamber walls may be formed separate from the compression surfaces, and other methods of creating the chamber will also be apparent to the skilled in the art.

Figure 14:
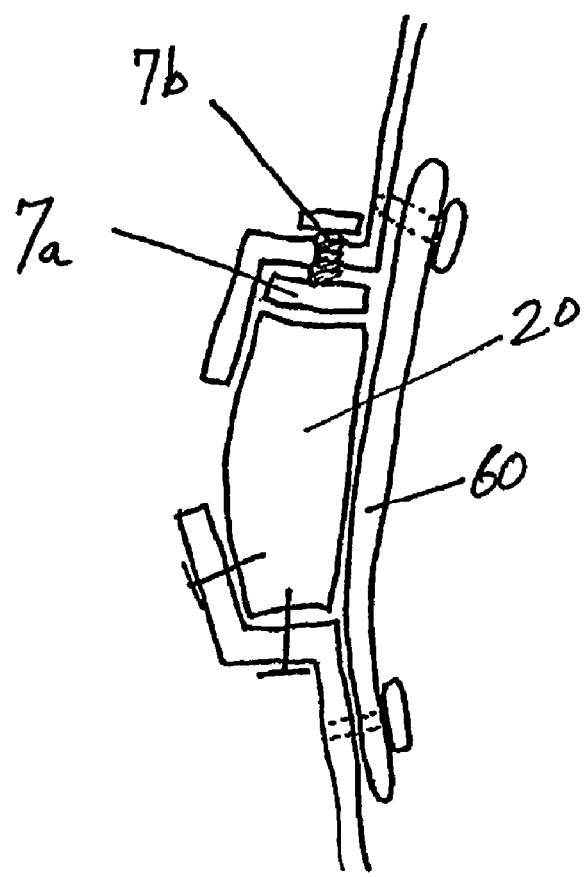
FIG. 14 depicts the cross section of the embodiment with an adjustable compression surface.

The compression surfaces are preferably flat, but may take any desired form as long as they are capable of transmitting the plantarflexion moment forces to the bumper. One or more of the compression surfaces may be adjustable as shown for example in FIG. 14 to allow fine tuning of the preload and/or the plantarflexion resistance. Such adjustability may be provided by screws 7b, cams, ratchets, or any other arrangement that will be known to the skilled in the art for varying the location of a surface 7a without compromising its load bearing capacity.

Preferably, the bumper consists of a piece of flexible material having relatively low modulus of elasticity. The modulus of elasticity is commonly known as 'durometer number' after a common instrument to measure the compressibility of the material. Materials such as rubber, silicone, urethane, polyurethane, surlyn™, foam, and the like, are but few examples of suitable bumper material. However alternative bumper construct may be used such as springs, jell cells, pneumatic containers, hydraulic cells, and other implements that provide elastic response to plantarflexion forces.

Preferably, the bumper is slightly oversized to the chamber size. Thus the unloaded foot portion of the brace is set at an acute angle to the calf section. The preload angle of the foot and calf sections may be adjusted by selecting bumpers of varying dimensions as regards to size and/or shape. While the bumper may be attached to the brace, compression walls or chamber, it is preferably floating, i.e. freely disposed, within the chamber. The preferred embodiment utilizes a compression fit into one half of the chamber and a looser fit into the other half. The floating bumper allows for inexpensive manufacturing and easy bumper replacement.

Figure 3:
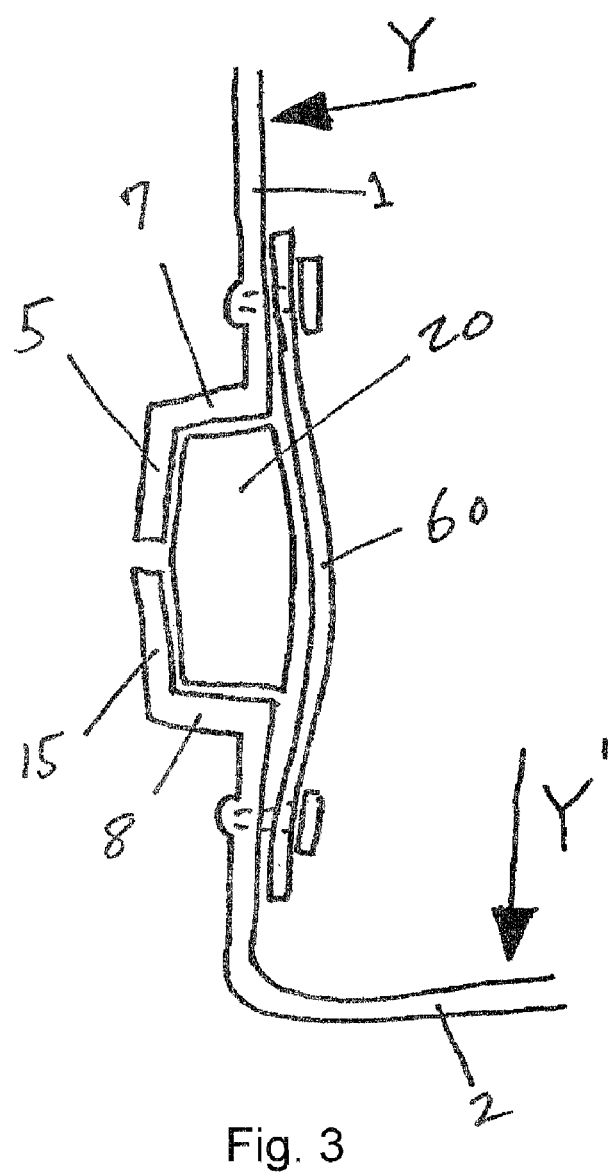
FIG. 3 depicts the joint of FIG. 2 in a compressed, or loaded state.

The tensor attaches the foot and calf portions, and carries the load applied by the foot. As shown in FIG. 3, during plantarflexion, the compression surfaces transmit the moment force applied by plantarflexion, as forces indicated by vectors Y and Y', to the bumper. As the bumper has a relatively low modulus of elasticity it allows a certain amount of compression and resists excessive plantarflexion. Thus the modulus of elasticity and the bumper dimensions allow adjustability of the resistance to plantarflexion.

Figure 5:
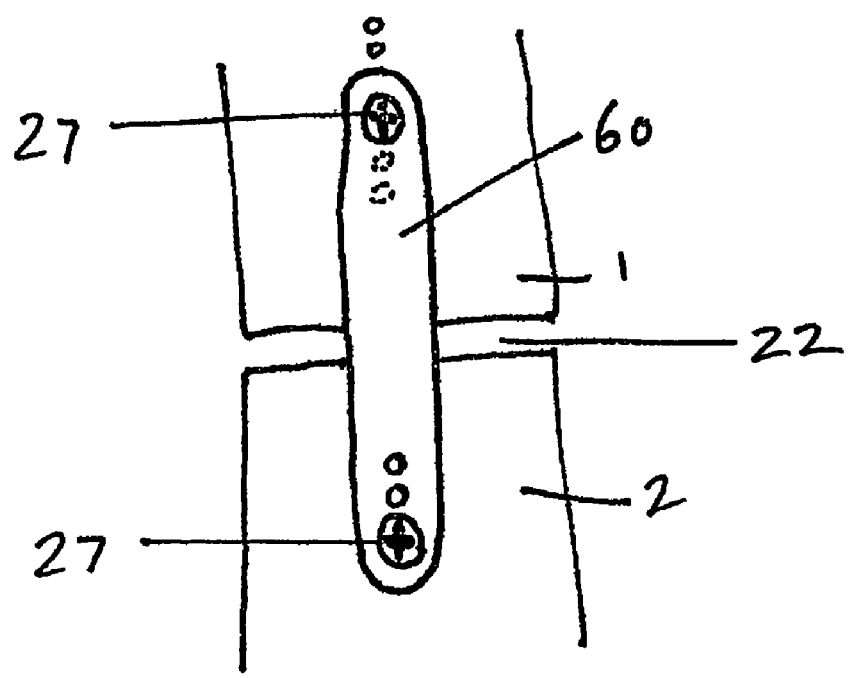
FIG. 5 depicts the front view of the joint of FIG. 2.

FIG. 3 depicts a side view of a joint according to a preferred embodiment during plantarflexion, with the bumper 20 in a compressed state. The bumper is partially enclosed by a chamber formed by pockets in the calf section 1 and in the foot section 2. As shown in FIGS. 1 and 5, the tensor 60 defines another boundary, or wall, of the chamber. The skilled in the art will recognize that the tensor is under tension load, while the bumper is under compression load. Therefore the tensor and bumper form a strong joint that provides full range of motion and simultaneously provides resistance to excessive platerflexion. As can be seen in FIG. 1, the preferred embodiment calls for the tensor to be placed on the interior surface of the brace and for the chamber to be formed in the exterior surface of the brace.

Figure 4:
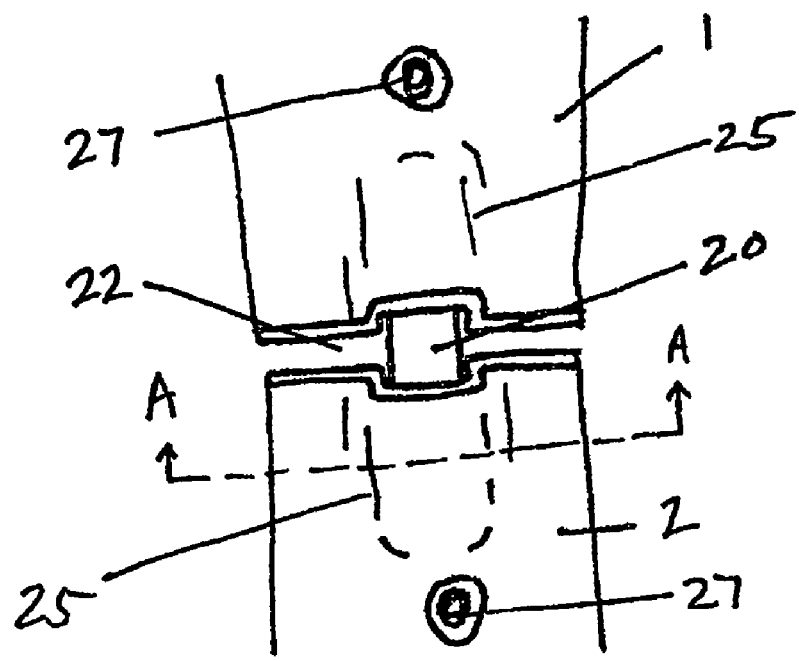
FIG. 4 depicts a rear view of the joint of FIG. 2.

FIG. 4 depicts the rear view of the preferred embodiment of the joint, and FIG. 5 provides a view of the front (preferably the one close to the foot). FIG. 5 also shows an optional way to adjust the effective length of the tensor by selecting one of a plurality of mounting holes serving as anchor points. Doing so allows for angular, lateral, or medial adjustment between the foot portion and calf portions. The skilled in the art will recognize that a similar method employing a plurality of mounting in the foot portion, the calf portion, or in both, will achieve equivalent result that is also within the scope of the invention. In both cases, it is preferred that the tensor anchor points are transverse to the flat side of the tensor.

Figure 6:
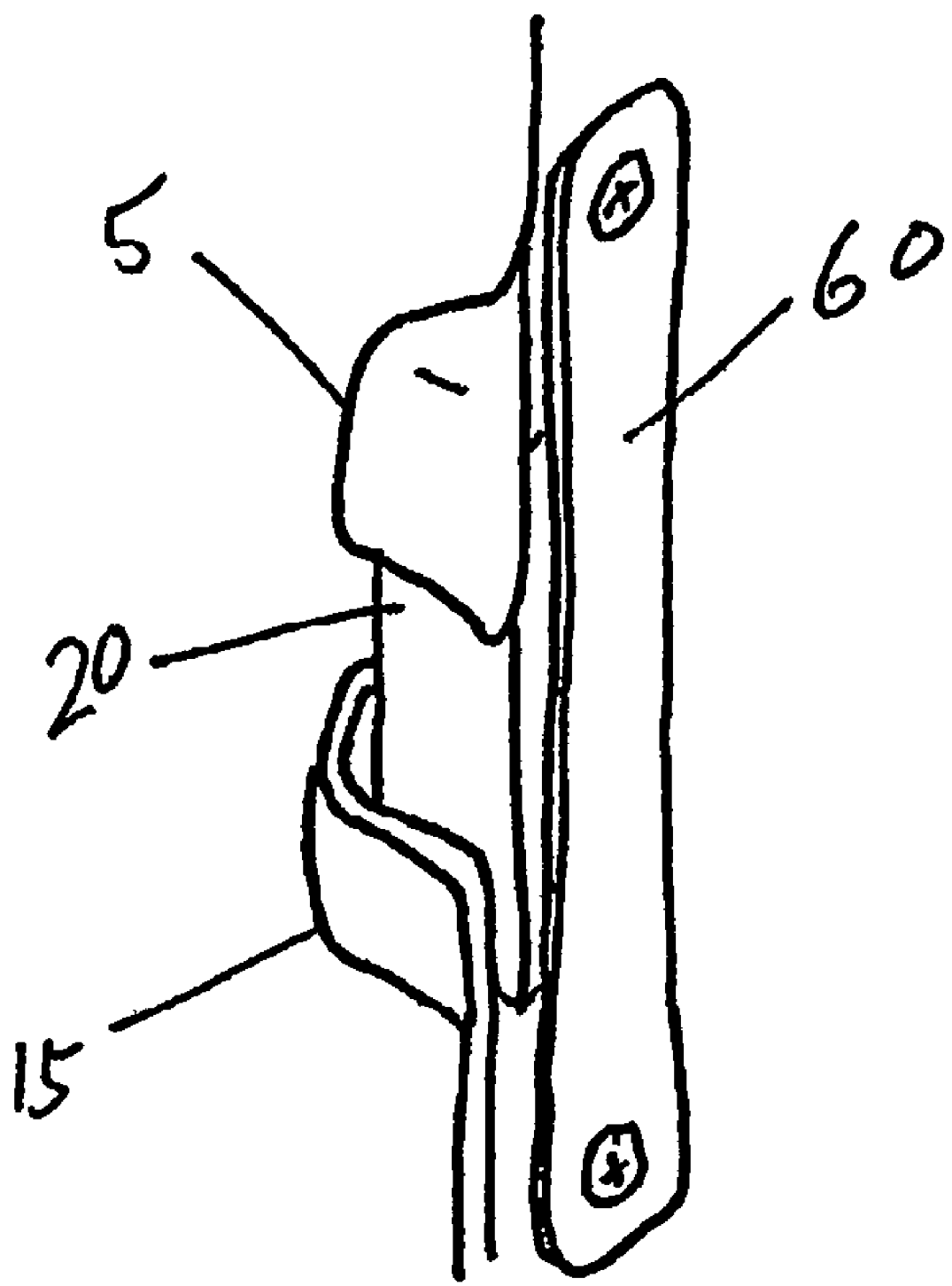
FIG. 6 depicts a perspective view of the joint of the previous figures.
Figure 7:
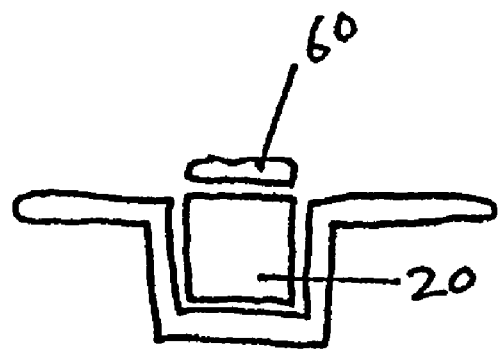
FIG. 7 depicts a cross section view along cutoff line AA in FIG. 4.

Preferably a gap 22 exists between the calf and foot portions. The inner chamber wall is depicted by a dashed line 25. Fasteners 27 are preferably used to attach the tensor to the foot and calf portions. FIG. 6 is a perspective view of the joint showing the tensor, bumper, and the chambers partially surrounding he bumper. FIG. 7 depicts a cross section of the joint at dashed lines AA in FIG. 4.

Figure 8:
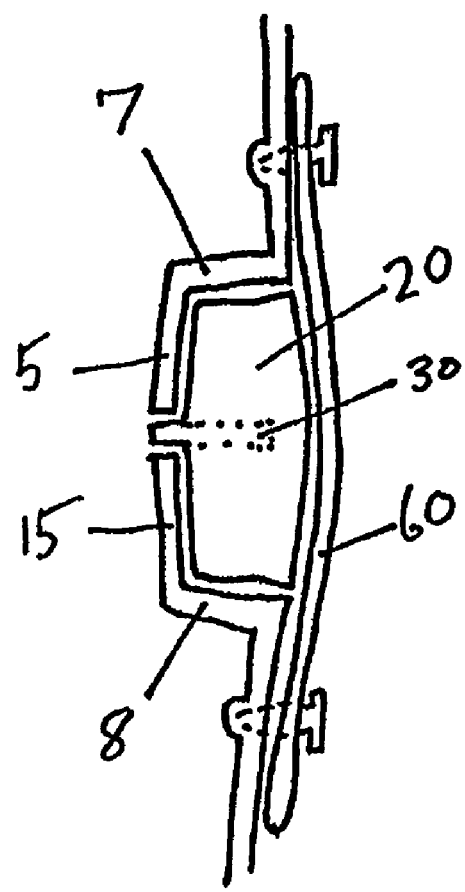
FIG. 8 depicts the joint of FIG. 3 with a motion limiter.

In certain cases for an AFO it is desirable to limit the maximum distance that the foot may travel, such as to prevent a drop foot. When one or more of the relatively rigid chamber walls meet, (such as the chamber outer walls 5 and 15) further motion is prevented, however such direct contact of the foot and calf portion may result in abrupt stop of the foot motion. FIG. 8 shows an example of a motion limiting arrangement that offers a more gradual motion limit by having the chamber walls 5 and 15 apply force to a stopper 30 having a higher modulus of elasticity, which results in increased resistance to excessive plantarflexion without the jarring motion two rigid parts coming into abrupt contact. Clearly, other placement of the stopper 30 and the respective surfaces applying forces thereto are possible, however the placement of the stopper in the vicinity or within the bumper are preferred as it places the stopper in proximity to the tensors and thus allow better force distribution.

Figure 9:
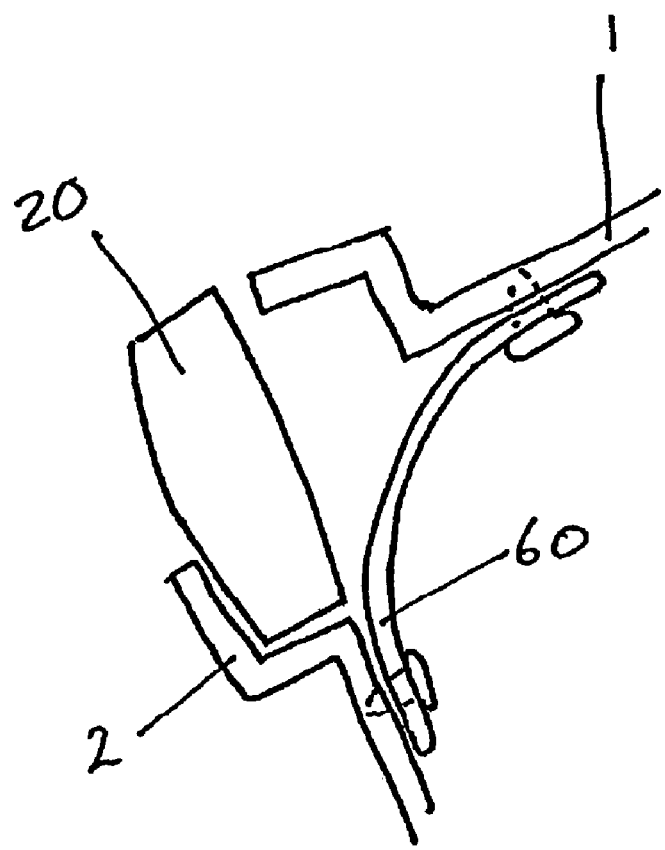
FIG. 9 depicts a cross section of the preferred embodiment, showing the tensor in an over-flexed state.

FIG. 9 is a cross section of the preferred embodiment, showing how bumpers may be replaced. A notable advantage of the preferred embodiments is the chamber, which allows the bumper to float freely therein, requiring no means of attachment of the bumper to the brace. This advantage eases field adjustability of the brace for the needs of individual patients, by simple replacement of the bumper. In order to replace the bumper, the two portions are angularly rotated about the tensor, creating a sufficiently large opening in the chamber to allow the bumper to be withdrawn. Therefor, in the most preferred embodiment, it is highly desirable to utilize a tensor having high tensile strength along the axis between its mounting points, and sufficiently flexible to allow resilient bending between the foot portion relative to the calf portion, thus allowing easy replacement of the bumper. To best achieve those goals in the present preferred embodiments, the tensor will have an overall bending stiffness in at least one axis, of between 0.035 and 1.3 Nm, where the range between 0.08 and 0.9 Nm is preferred. Presently, it is believed that the ideal range is between 0.2 is 0.5 Nm.

Figure 13:
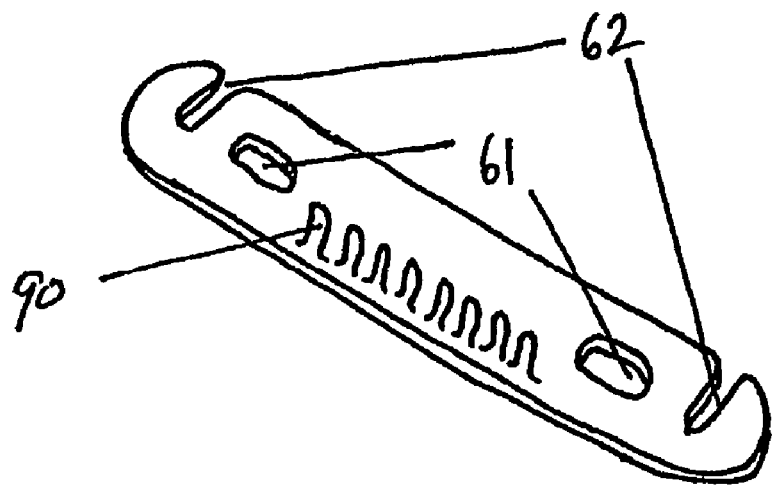
FIG. 13 depicts an alternative tensor construction.
Figure 10:
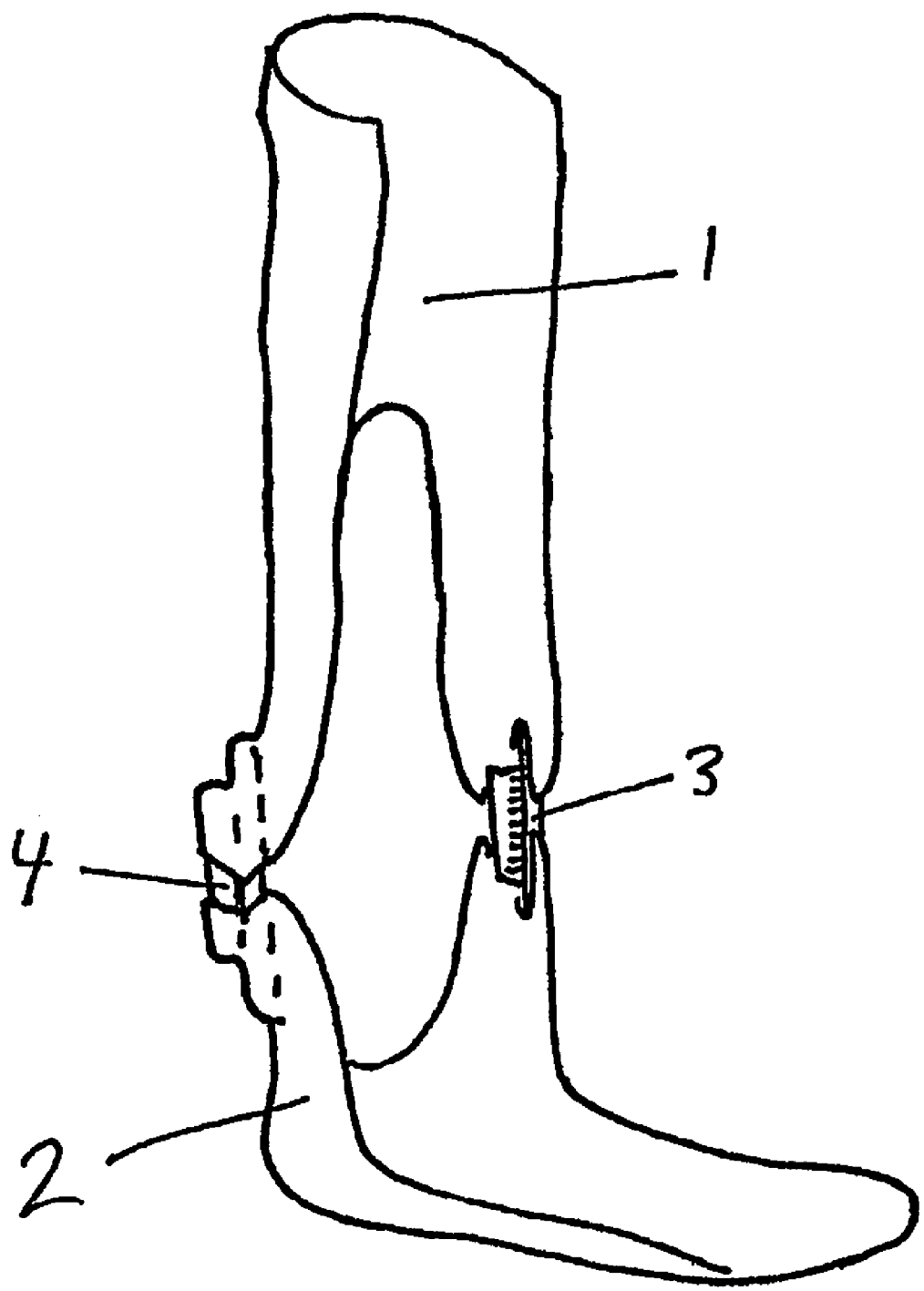
FIG. 10 depicts another preferred embodiment of the joint.
Figure 11:
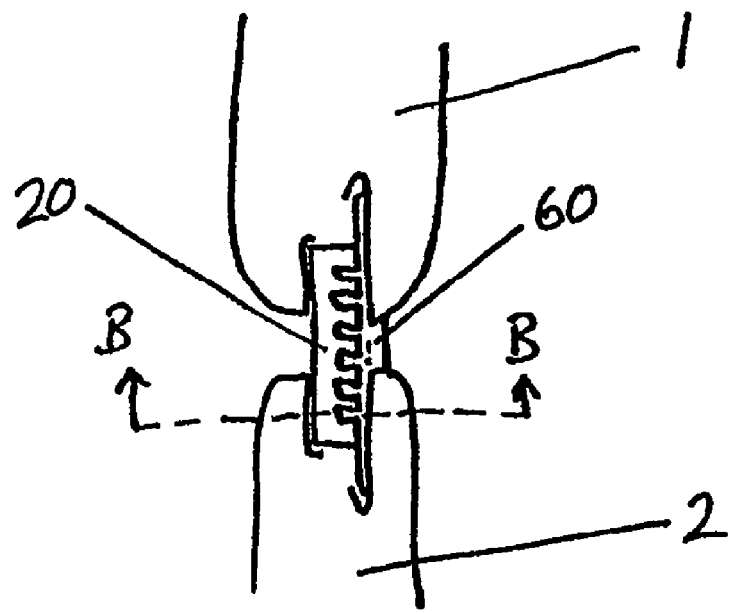
FIG. 11 shows the alternative design of FIG. 10 as applied to an AFO.
Figure 12:
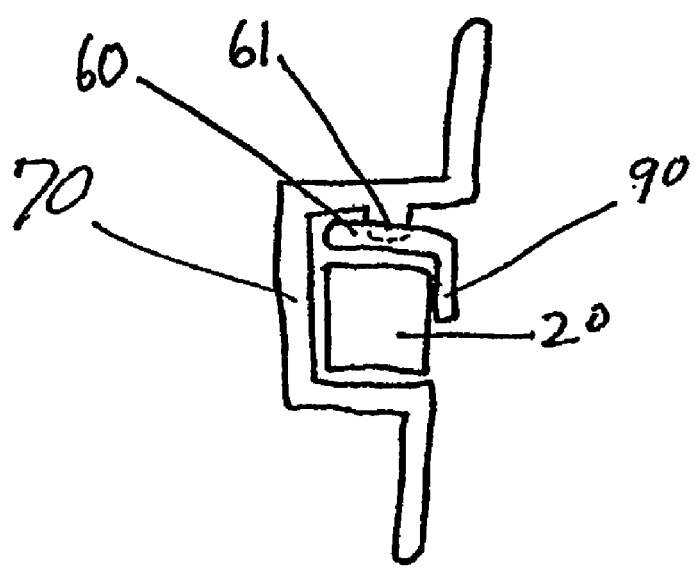
FIG. 12 depicts a cross section view along line BB in FIG. 11.

In certain cases it is advantageous to place the hinges near ankle. FIG. 10 shows a brace with such placement. Furthermore, the joint depicted in FIG. 10 is of an alternative design, details of which are shown on FIGS. 11, 12 and 13. In this embodiment, the bumper and the tensor are both inserted from the inside of the brace. Tensor 60 is inserted inside the chamber, alongside the bumper 20, as can be seen in FIG. 12 which is a cross section along the lines BB in FIG. 11. In order to maintain the bumper 20 in position, the tensor in this embodiment is shaped with a bumper holder 90. The bumper holder may be any protrusion extending to hold the bumper in place, however the preferred embodiment uses fingers that are bent about 90 degrees to the plane of the tensor as seen in FIG. 13.

Optionally, this embodiment offers yet another advantage: if desired, the tensor may have slots 62 cut therein that interact with protrusions (not shown) in the calf and foot portions of the brace, to achieve anchoring. Such arrangement provides easy anchoring of the tensor and the tension forces are transferred to the tensor via the slots. The slots obviate the need for fasteners and therefore reduce the cost of manufacture. Holes 61 are preferably cut into the tensor and engage with matching teeth in the brace to hold the tensor in place.

Figure 15:
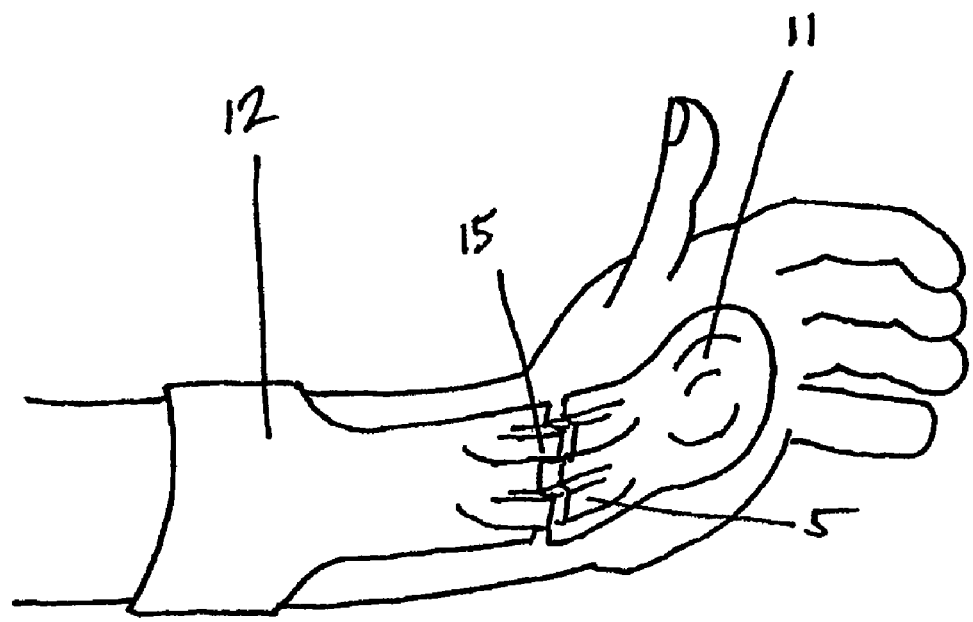
FIG. 15 depicts another embodiment of the invention as it relates to the wrist and hand.

FIG. 15 shows an embodiment of the invention as it may be applied to a wrist hand orthosis. The upper forearm section 12 is hingedly connected to the lower hand section 11. The skilled in the art will recognize that the operation of the joints as described above between the calf and foot portions will be equivalently applicable to the operation of such joints between the forearm and wrist sections. Therefore while the majority of the description related to the AFO example, the scope of the claims clearly extends to the wrist hand orthosis and other similar orthosis types.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. An articulated orthosis having a first and a second hinged shell parts, the orthosis having an inner and outer surfaces, and at least one joint for hinging the first and second shell parts, the orthosis comprising:
  a tension element having a first anchor point coupled to the first hinged shell part and a second anchor point coupled to the second hinged shell part, the tension element having at least one generally flat outer surface which is substantially co-planar to the inner surface of the orthosis adjacent to the tension element;
  a first and a second compression surfaces coupled to the first and second shell respectively;
  a compression element comprising a first block of resilient material, disposed between the compression surfaces;
  wherein the compression surfaces are located so as to transmit forces to the compression element as a result of angular motion between the first and second hinged shell parts, the forces being operable to compress the compression element;
  wherein the compression element and tension elements form a joint which is located posteriorly and superiorly to an anatomical joint.

2. An articulated orthosis as claimed in claim 1, wherein said tension element has an overall bending stiffness in the range between 0.02 and 1.3 Nm.

3. An articulated orthosis as claimed in claim 1, wherein at an unloaded condition the angle between the first and second hinged shell parts is variable by the dimensions of the compression element.

4. An articulated orthosis as claimed in claim 1, wherein resistance to moment force applied to at least one of the hinged shell parts is variable by the modulus of elasticity of the compression element.

5. An articulated orthosis as claimed in claim 1, wherein the tension element has an adjustable effective length, for allowing relative angular adjustment of the hinged shell parts.

6. An articulated orthosis as claimed claim 1, wherein at least one of the hinged shell parts has a plurality of retaining walls for forming a chamber to at least partially contain the compression element, and wherein the tension element defines a boundary of the chamber.

7. An articulated orthosis as claimed in claim 6 wherein at least one of said retaining walls is movable for changing the dimensions of the chamber.

8. An articulated orthosis as claimed in claim 6 wherein the compression element is freely disposed within the chamber.

9. An articulated orthosis as claimed in claim 1, wherein at least one of said compression surfaces is adjustable.

10. An articulated orthosis as claimed in claim 1, wherein the compression element further comprises a second block of resilient material having a higher modulus of elasticity than the modulus of elasticity of the first block, the second block disposed between at least a portion of the first and second hinged shell parts, so as to be compressed as result of angular motion therebetween, after compression has been applied to the first block.

11. An articulated orthosis as claimed in claim 1, wherein the tension element comprises anchor points transverse to the flat side.

12. An articulated orthosis as claimed in claim 1, wherein the compression surfaces are integral to at least one of the hinged shell parts.

13. An articulated orthosis as claimed in claim 1, wherein the compression element is selected from a list consisting of a, jell cell, pneumatic container, hydraulic cell, or a combination thereof

14. An articulated orthosis as claimed in claim 1, wherein said tension element has an overall bending stiffness of between 0.08 and 0.9 Nm.

15. An articulated orthosis as claimed in claim 1, wherein said tension element has an overall bending stiffness of between 0.2 and 0.5 Nm.

16. An articulated orthosis as claimed in claim 1, wherein at least part of the tension element is integral to one of the hinged shell parts.

\* \* \* \* \*